(12) United States Patent
Newkome

(10) Patent No.: US 7,772,431 B1
(45) Date of Patent: Aug. 10, 2010

(54) PERFORMANCE OF ENERGY STORAGE DEVICES: POTENTIAL AREAS FOR DENDRITIC CHEMISTRY INVOLVEMENT

(76) Inventor: George R. Newkome, 200 Granger Rd. #92, Medina, OH (US) 44256-7322

( * ) Notice: Subject to any disclaimer, the term of this patent is extended or adjusted under 35 U.S.C. 154(b) by 557 days.

(21) Appl. No.: 11/750,448

(22) Filed: May 18, 2007

Related U.S. Application Data

(60) Division of application No. 10/049,259, filed on Apr. 23, 2002, now Pat. No. 7,250,534, which is a continuation-in-part of application No. PCT/US00/40431, filed on Jul. 20, 2000.

(60) Provisional application No. 60/145,785, filed on Jul. 27, 1999.

(51) Int. Cl.
*C07C 233/18* (2006.01)
*C08G 18/02* (2006.01)

(52) U.S. Cl. .................... 564/153; 525/452; 564/197

(58) Field of Classification Search .................. 564/153, 564/197; 525/452
See application file for complete search history.

(56) References Cited

U.S. PATENT DOCUMENTS 5,773,551 A * 6/1998 Newkome et al. ............. 528/69

* cited by examiner

*Primary Examiner*—Charanjit S Aulakh
(74) *Attorney, Agent, or Firm*—Kohn & Associates, PLLC

(57) ABSTRACT

A compound consists of a fractal-like, plain or organometallic array useful for energy storage devices. A dendrimer useful in the synthesis of the fractal-like compound includes a single ligating moiety bound to a surface of each quadrant of the dendrimer. A method of making metallo-based (macro) molecules includes the steps of combining monomers selected from the group consisting of bipyridal- and terpyridal-based ligands with connecting metals and self assembling macrocycles wherein the monomes are interconnected by the metals.

3 Claims, 11 Drawing Sheets

PERFORMANCE OF ENERGY STORAGE DEVICES: POTENTIAL AREAS FOR DENDRITIC CHEMISTRY INVOLVEMENT

CROSS-RELATED REFERENCE SECTION

This application is a Divisional application of U.S. patent application Ser. No. 10/049,259, filed Apr. 23, 2002 now U.S. Pat. No. 7,250,534, which is a National Phase Continuation-In-Part Application of International Application No. PCT/US00/40431, filed Jul. 20, 2000, which claims the benefit of priority under 35 U.S.C. Section 119(a-d) of U.S. Provisional Patent Application Ser. No. 60/145,785, filed Jul. 27, 1999, all of which are incorporated herein by reference.

TECHNICAL FIELD

The present invention relates to dendritic materials for use in energy storage devices. More specifically, the present invention relates to branched macromolecules for use as enhanced electrolyte and electrocomponents in solid state energy storage devices.

BACKGROUND OF THE INVENTION

The present invention relates to the melding of iterative synthetic protocols with more mature research arenas for the production of utilitarian materials. Accordingly, the present invention combines the areas of dendrimers, combinatorial chemistry, and dendrimer-based electrolyte material chemistry and applies the same to the utilitarian arena of electrocomponents and enhanced electrolyte capability in solid state energy storage devices. Hence, each of these fields is addressed as the present invention provides improvements resulting from a synergy of advancements in each of these fields in combination.

By way of background, rapid advancement in the field of "dendritic chemistry" (Newkome at al., VCH: Weinheim, Germany, 1996) has afforded scientists with a new arsenal of techniques for the construction of utilitarian materials. Testament to interest in this burgeoning area is evidenced by ubiquitous literature reports on the subject since its discovery (1978) and commencing rise (mid-1980s). Central to dendritic chemistry is the "iterative synthetic methodology", which has afforded new pathways to the construction of complex, high molecular weight molecules.

The realization of "dendrimers", and related constructs such as "hyperbranched" polymers (Hult et al., 1999) and "dendrimer-polymer hybrids", (Roovers et al., 1999) has thus facilitated advances in the ability to design and build architecturally homogeneous branched molecular assemblies.

There are inherent limitations imposed on these structures due primarily to 1) the repetitive application of a single building block for tier construction leading to functional group uniformity on the surface, as well as the interior, of the branched structure and 2) a lack of interchangeable monomers that would facilitate the incorporation of diverse application oriented functionality and thus allow the creation of utilitarian assemblies.

These limitations are addressed via 1) the development of a "modular" set of application-oriented branched building blocks for dendritic synthesis (Young et al., 1994) aimed directly at enhanced solid-state energy storage and release devices (e.g., lithium battery performance); 2) the use of combinatorial-based tier construction techniques (Newkome et al., Isocyanate-Based Dendritic Building Blocks: Combinatorial Tier Construction and Macromolecular Property Modification, Angew. Chem., Int. Ed. Engl., 1998) for the creation of unimolecular, multi-component assemblies whereby the individual components can act in concert to produce a desired physiocochemical effect, and 3) use of branched architectures to fabricate, template, and stabilize metal and non-metal particles, composites, and clusters.

Specifically, advancement in lithium- and lithium rocking chair-battery efficiency (Lipkowski et al., 1994; Owen, J. R., 1997) is shown to result from 1) improved electrolyte materials based on highly stable, polyethylene glycol functionalized, saturated hydrocarbon-type dendrimers, and 2) significantly reduced inter-electrode separations. Ultimately, this has led to branched assemblies possessing mutually compatible and synergistic units capable of triggered electrochemical discharge. This forms the basis of a logical evolution of iterative chemistry that melds the maturity of classical polymer, organic, and inorganic chemistries, as well as emerging fields that include "$C_{60}$" technology, with the strengths of dendritic chemistry.

To date, a diverse set of branched monomers have been crafted for the introduction of 1) high-density surfaces and 2) "latent" functionality to be used, or activated, after primary dendritic construction, including: terpyridine (Newkome, et al., J. Mater. Chem. 1997; Newkome et al., Chem. Commun. 1998) arylamne hexaester, (Newkome et al., Synlett 1992) arylaminoterpyridyltriester, (Newkome et al., Chem. Commun. 1999) and arylnitroanthraquinonoid (Narayanan et al., 1999; Newkome et al., Designed Monomers and Polymers, 1999; Newkome et al., Macromolecules, 1999; Newkome et al., Macromolecules, 1997).

Additionally, applicants have recently reported the preparation of β-cyclodextrin branched building blocks has recently reported (5) for use in self-assembly studies predicated on molecular recognition and host-guest inclusion. (Newkome et al., Chem. Commun., 1998).

A novel family of isocyanate, 1→3 branched buildings blocks has been developed and reported (Newkome et al., U.S. Pat. No. 4,154,853, 1992; Newkome et al., Angew. Chem., Int. Ed. Engl., 1991; Newkome et al., Chem. Commun., 1996; Newkome et al., Tetrahedron Lett., 1997; Newkome et al., Designed Monomers and Polymers, 1997) that allows 1) rapid physiocochemical modifications of diverse macromaterials (Newkome et al., Chem. Commun., 1996) and 2) "combinatorial-based" multiple functional group incorporation. (Newkome et al., Combinatorial Chem., 1999; Newkome et al., U.S. Pat. No. 5,886,126, 1999; Newkome et al., U.S. Pat. No. 5,886,127, 1999). Each member of this series relies on an isocyanate moiety for monomer connectivity. Steric demands associated with the adjacent branch junctures give rise to unprecedented isocyanate stability. These materials are generally solids that are stable in air, which facilitates handling and storage. For example, the isocyanatotriester is a white crystalline soli (mp 60-62° C.) that reacts readily with amines and requires slightly more vigorous conditions to react with alcohols; its crystal structure has been reported. (Newkome et al., Tetrahedron Lett., 1997).

Eloquent work in the area of self-assembly by Stang (1), Lehn (2), and many others (3-7), has prompted our investigation of the potential to spontaneously construct Ru-based (macro)molecules. More specifically, our goal involved the design and preparation of polyterpyridyl ligands that would form the basis of a "modular building block set" (8) capable of being used to access "higher order" (fractal) architectures. We herein report the construction of a bis(terpyridine) monomer that facilitates the preparation of hexaruthenium macrocycles.

Linear bis(terpyridyl) monomers have been employed for the formation of layered polyelectrolyte films (9), Ru(II)-based dendrimers (10), helicating ligands (11), grids (12), racks (13), and photoactive molecular-scale wires (14), to mention but a few. Whereas, progress in directed synthesis of cyclic rigid structures can be found in "shape persistent" phenylacetylenes (15-17), diethynylbenzeme macrocycles (18), and a 24 phenylene hexagon (19), advances via self-assembly has yielded, for example, chiral (20) and achiral (21) circular helicates, cylindrical cage structures (22), Pt-coordinated bipyridyl squares (23), and metal-templated [2]catenanes (24, 25), and cyclic porphyrin trimers (26).

In view of the above, it is desirable to develop further compounds, and in the larger sense, various means for improving and enhancing electrolyte and electrocomponents in solid state, energy storage devices. It would be desirable to be able to meld together iterative processes utilized in dendritic chemistry with combinatorial processes which have also been highly developed in dendritic chemistry towards multiple unit positioning within dendritic structures and other architectures in order to obtain improvements and enhancements.

SUMMARY OF THE INVENTION

According to the present invention, there is provided a compound of the formula

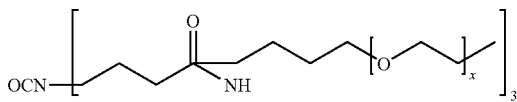

wherein x is an integer from 1 to 4.

A method of making dendrimer frameworks includes the steps of reacting and converting a triethylene glycol and then coupling it and subsequently reducing the building block, followed by forming a dendrimer core and reacting the building block with the dendrimer core to yield a first generation dendrimer.

The present invention further provides a monomer of the formula

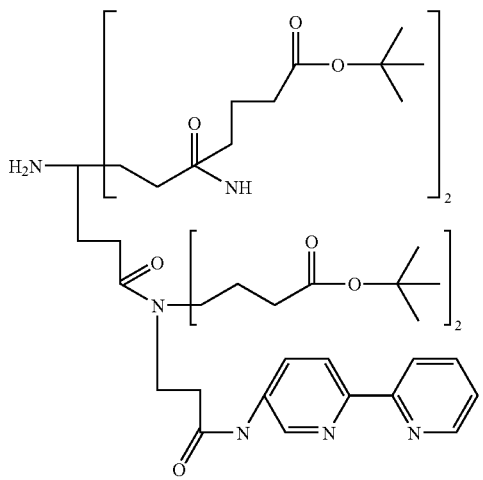

More generally, a dendrimer is provided including a single ligating moiety bound to a surface of each quadrant of the dendrimer.

A dendrimer is further provided which is a nanocrystallite.

A method of making metallo-based (macro)molecules includes the steps of providing monomers selected from the group consisting of bipyridal- and terpyridal-based ligands with connecting metals and self-assembling macrocycles wherein the monomers are interconnected by the metals.

Finally, a compound is provided which consists of a fractal-like, planar organometallic array.

BRIEF DESCRIPTION OF THE DRAWINGS

Other advantages of the present invention will be readily appreciated as the same becomes better understood by reference to the following detailed description when considered in connection with the accompanying drawings wherein.

DETAILED DESCRIPTION OF THE INVENTION

Generally, the present invention provides several generic concepts and several further specific compounds and methods of making compounds, all in combination significantly advancing the art of electrolyte and electrocomponents in solid state, energy storage devices. The methods disclosed below are useful for manufacturing either monomers used as building blocks to create compounds or the compounds per se, which are useful as electrolytes in energy storage devices. Such compounds useful in energy storage devices are capable of encapsulating, entraining, and stabilizing metal and non-metal nanoclusters for use in electromaterials and surfaces. Such materials, by use of combinatorial-based synthetic techniques, are disclosed herein which allow for the preparation and rapid testing of heterogeneously functionalized branched assemblies with tunable physiochemical properties. Such tunable physiochemical properties allow for the maximization of enhanced electrolyte capability of stackable compounds capable of energy storage and release through the metals retained thereby.

Figure 1:
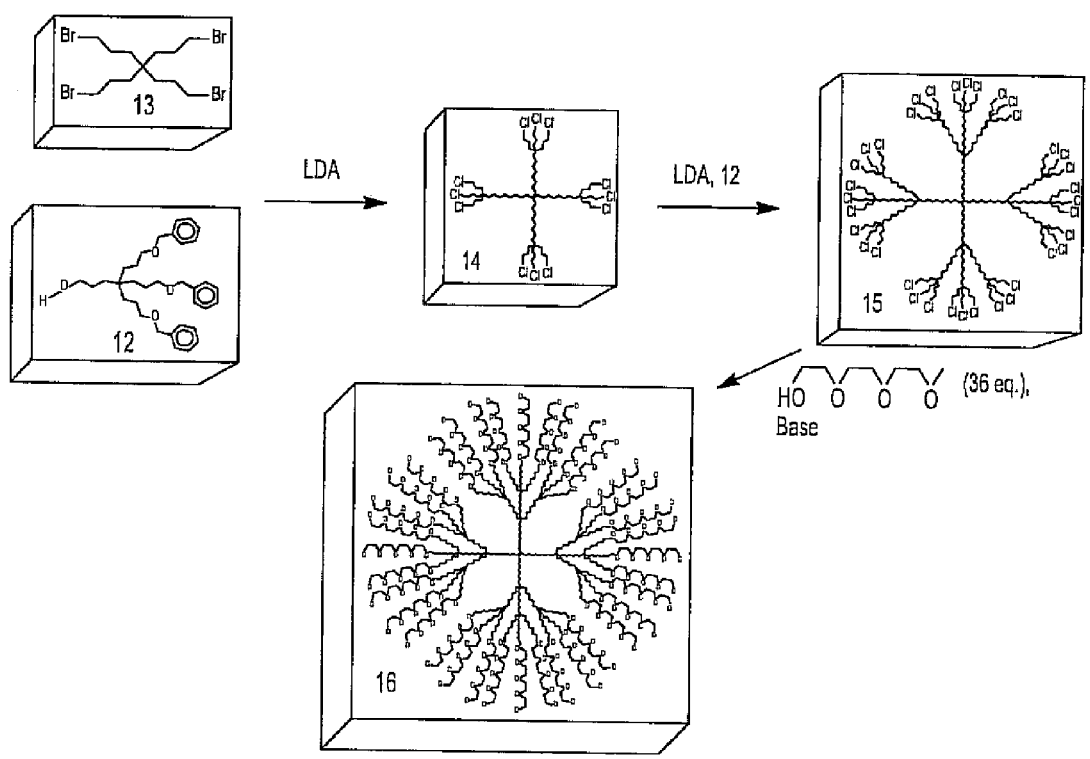
FIG. 1 shows the construction of PEG-terminated hydrocarbon-based dendrimers.

While numerous routes and electrolyte architectures can be envisioned, four approaches are described which allow access to these materials. More specifically, dendritic polymer-based electrolyte materials, as shown in FIG. 1, are predicated on the use of the process for construction of all-saturated hydrocarbon dendrimers (Newkome et al., U.S. Pat. No. 5,154,853, 1992; Newkome et al., Unimolecular micelles, Angvew. Chem., Int. Ed. Engl., 1991; Newkome et al., Alkane Cascade Polymers Possessing Micellar Topology: Micellanoic Acid Derivatives, Angew. Chem., Int. Ed. Engl. 1991) (i.e., 14 and 15 that are prepared from monomers 12 and 13 via sequential alkylation, reduction, and halogenation) and the attachment of polyethylene glycol units on the dendrimer surface. Polyethylene glycol (PEG) units can be easily attached to dendrimers and building blocks via the well established Williamson synthesis (Beckmann et al., 1981; Burns et al., 1999) to afford PEG-modified dendrimers (16). Examination of these materials in concert with added "free" salts (Lipkowski et al., 1994; Owen, J. R., 1997; Salomon, M., 1998; Cisak et al., 1993) [e.g., $LiClO_4$, $LiCF_3SO_2$, $LIPF_6$, $LiN (SO_2CF_3)_2$, and $LiC (SO_2CF_3)_3$] is planned. PEG commercial availability allows access to a variety of chain lengths.

Saturated hydrocarbon frameworks are effectively inert towards oxidizing and reducing conditions. Hence, it is expected that improved electrolyte stability, more efficient Li-ion transport, and decreased electrolyte layer thickness will result in greater specific energy, energy density, and battery cycle life. (Owen, J. R., 1997) Specific present pitfalls (Lipkowski et al., 1994) addressed by this technology are (a) stability towards highly oxidizing and reducing environments [i.e., at the anode and cathode interfaces due to the absence of reactive functional groups such as NH, OH, etc.]; (b) electrolyte crystallinity and brittleness [i.e., such as found with LiI and some other polymeric matrices]; (c) mechanical strength; (d) charge and discharge temperature range operation; (e) electrolyte layer thickness [inter-electrode gaps corresponding to ~$10^{-8}$ to $10^{-9}$ m are envisioned assuming a dendrimer radius of 20-25 Å]; (f) lithium plating ['dendrite' formation should be reduced in a more electrochemically stable electrolyte region]; and (f) safety [environmental as well as operational].

Figure 2:
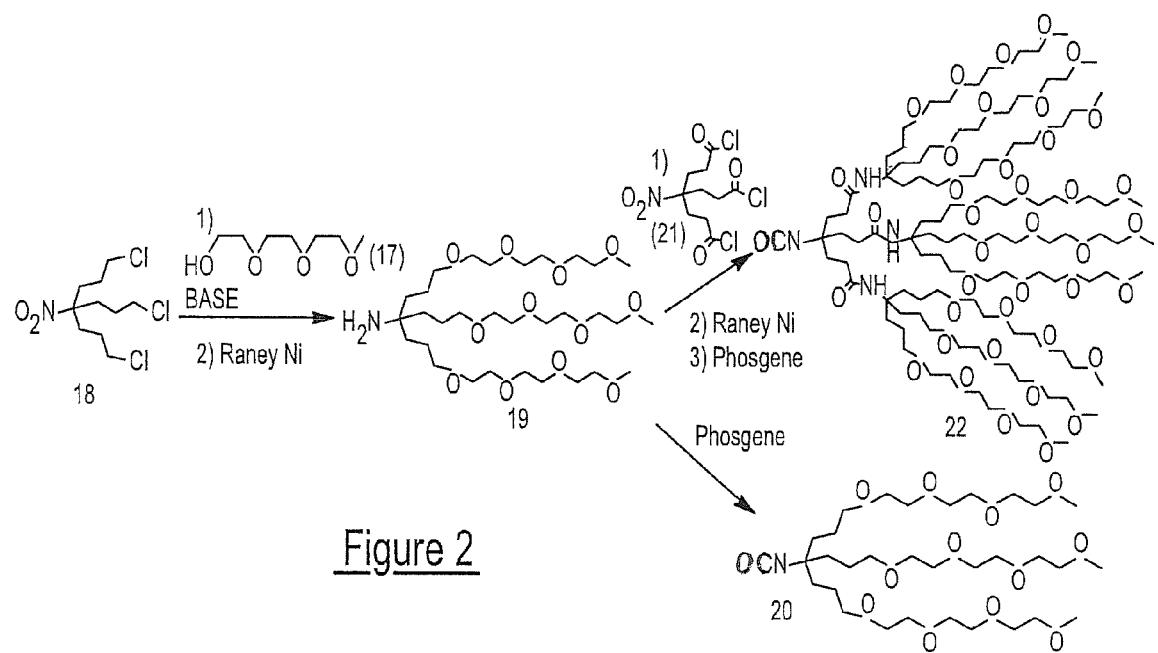
FIG. 2 shows the preparation of isocyanate-based, branched PEG monomers.

Synthesis of Branched PEG Architectures is Shown in FIG. 2. Monomers allowing for attachment of the polyether moieties to a wide array of surfaces and preconstructed dendrimers are prepared by employing the branched monomer design and isocyanate technology. (Newkome et al., Isocyanate-Based Dendritic Building Blocks: Combinatorial Tier Construction and Macromolecular Property Modification, *Angew. Chem., Int. Ed. Engl.* 1998; Newkome et al., *Designed Monomers and Polymers,* 1997; Newkome et al., U.S. Pat. No. 5,773,551, 1998) For example, monomethylated triethylene glycol (17: prepared via reaction of the glycol with 1 equivalent of MeI) can be reacted with the known nitrotrichloride (18) (Newkome et al., *Synthesis,* 1991) to give the nitrotris (triethylene glycol) (not shown) that can be reduced to afford the corresponding amine 19. Treatment of this amine with phosgene (or a phosgene equivalent such as di- or triphosgene) yields isocyanate 20. A second generation dendron can be accessed via coupling of amine 19 with nitrotris (acid chloride) 21. Subsequent reduction of the nitro moiety and treatment with phosgene gives an isocyanate monomer possessing 9 PEG units (22).

Figure 3:
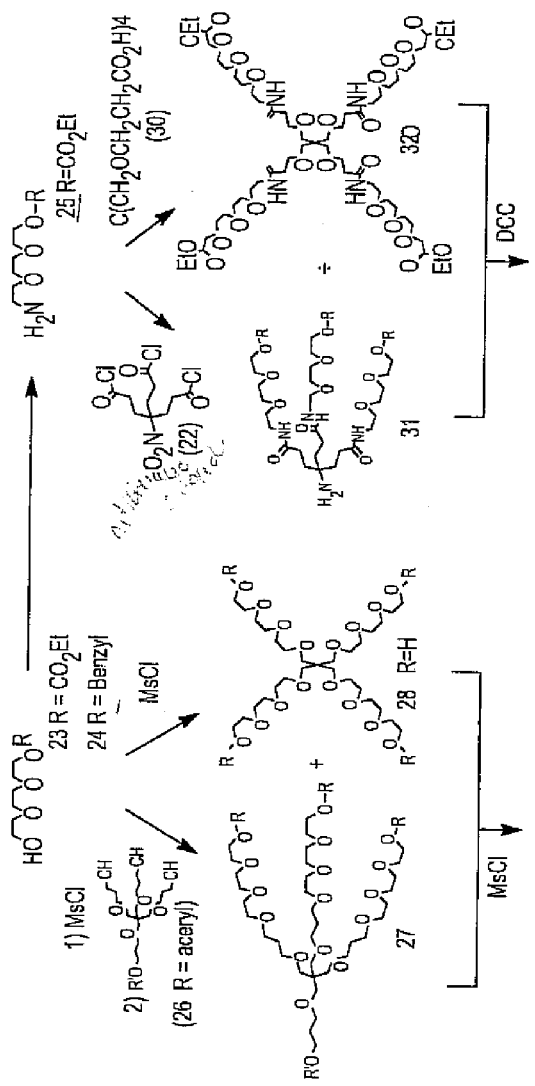
FIG. 3 shows the synthesis of PEG dendrimer framework.
Figure 3:
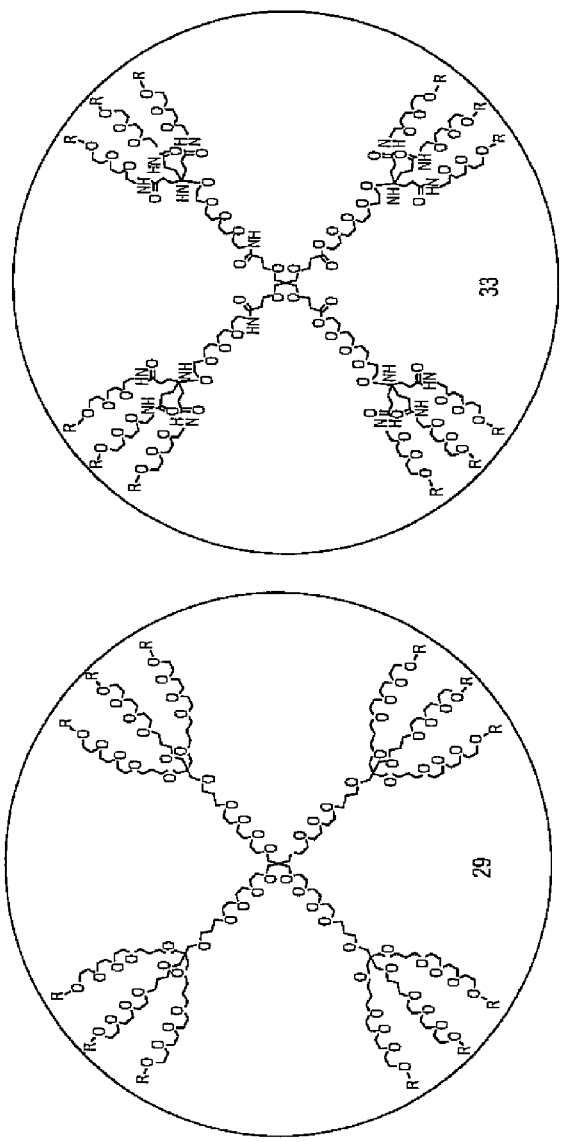

Tritethylene glycol units were prepared possessing terminally modified, complementary reactive and inert moieties (FIG. 3). Triethylene glycol was reacted separately with ethyl diazoacetate and benzyl chloride to afford ester 23 and benzyl ether 24, respectively. The free hydroxyl group of monofunctionalized glyco (23) was then converted to the corresponding amine via established procedures. Thus treatment of alcohol 23 sequentially with mesyl chloride (MsCl) and sodium azide ($NaN_3$) followed by catalytic hydrogenation (Pd—C, $H_2$) yielded amine 25.

PEG-based dendrimers, possessing polyether units throughout the dendritic structure, are accessible via use of these modified polyethers. For example transforming alcohol 24 to the 1→3 branched monomer 27 via conversion of 24 to the mesylate and reaction triol 26 (obtained by reduction of the corresponding tetraacid followed by treatment with one equivalent of acetyl chloride; a monosubstituted pentaerythritol can also be employed). Reaction of the same mesylate with pentaerythritol followed by reductive debenzylation should yield core 28. Basic deprotection of the acetyl moiety on monomer 27, transformation to the mesylate, and attachment to tetraol 28 provides the first tier polyether dendrimer 29. Repetition of the sequence allows access to higher generations.

In a complementary scheme, PEG-based dendrimer 18 is constructed using amide-based monomer connectivity. Amide versus ester based connectivity was chosen due to the greater stability of the C(O)—N bond. Thus, coupling aminoester 25 with nitrotris(acid chloride) 21 and subsequently reducing the nitro group should afford aminotriester 31. The corresponding core 32 can then be accessed by reaction of the traacid 30 with four equivalents of amino 25. Selective ester hydrolysis of core 32 followed by coupling of monomer 31 is anticipated to yield the first generation dendrimer 33.

Based on the high yields (generally 80-90%) of the reactions to access the building blocks and dendrimers in Scheme 3 and the commercial availability of diverse polyethylene glycol homologs, a wide latitude in structural design is attainable.

In view of the above, the present invention provides novel PEG dendrimer frameworks and methods of making the same. It should be noted that such methods can be utilized in homologous synthesis; that is, such methods can be utilized to synthesize homologues by modifications of a method well known in the art.

Further, the above methods demonstrate the ability of the present invention to produce a wide array of surfaces and preconstructed dendrimers employing branched monomer design and isocyanate technology developed by applicants. Such compounds can have a flat architecture capable of stacking, such being inert towards oxidizing and reducing conditions. Thus, they can provide improved electrolyte stability and more efficient Li-ion transport and decreased electrolyte layer thickness. This results in greater specific energy, energy density, and battery cycle life, as demonstrated by the prior art discussed above.

The present invention further provides combinatorial methods utilized toward the synthesis of multiple unit positioning.

While intra- and inter-molecular "multiple structural element positioning" is in its infancy, foundations rooted in such areas as molecular recognition and other non-covalent interactions suggest a host of potential architectures. For example, structural units can be held in precise juxtaposition via rigid control units (Zhang et al., 1992; Zhang et al., 1994) that bind branched units via H-bond-based molecular recognition (Newkome et al., *Chem. Commun.*, 1996) or, more simplistically, an 'event' (chemical or physical) can be effected via absorption of molecular guests that fill internal void regions and cause branch chain movement. A simple analogy is found in well known polymer swelling. Competition for binding sites and compartments can form the basis for "molecular triggers."

Additionally, a fundamental property of branched macromolecules that is useful for the construction of "next generation" materials is revealed via consideration of the allowed bond rotations (torsions) within these structures. (Newkome et al., *Combinatorial Chem.*, 1999, in press) This suggests molecular surfaces that are "dynamic" whereby terminal units can at one instant be separated as far as physically possible and in another moment these same units are nearest adjacent neighbors. Essentially, movement of terminal groups or units about the surface of the branched superstructure is predicated on simple bond rotations which can be effected by "logical constants." This dynamic property, which conceptually imparts a "Rubik's sphere" character to these unique molecules, can be controlled by the use of logical constraints (i.e., site-specific molecular recognition, disruption of internal H-bonding, swelling in void regions, etc.) to facilitate construction of macromolecular assemblies with controllable functional unit positions.

"Combinatorially" prepared structures (Newkome et al., Isocyanate-Based Dendritic Building Blocks: Combinatorial Tier Construction and Macromolecular Property Modification, *Angew Chem., Int. Ed. Engl.*, 1998; Newkome et al., *Combinatorial Chem.*, 1999) whereby tiers are constructed by using a mixture of equally reactive, complementary monomers are integral elements for the ultimate construction of tunable networks.

Figure 4:
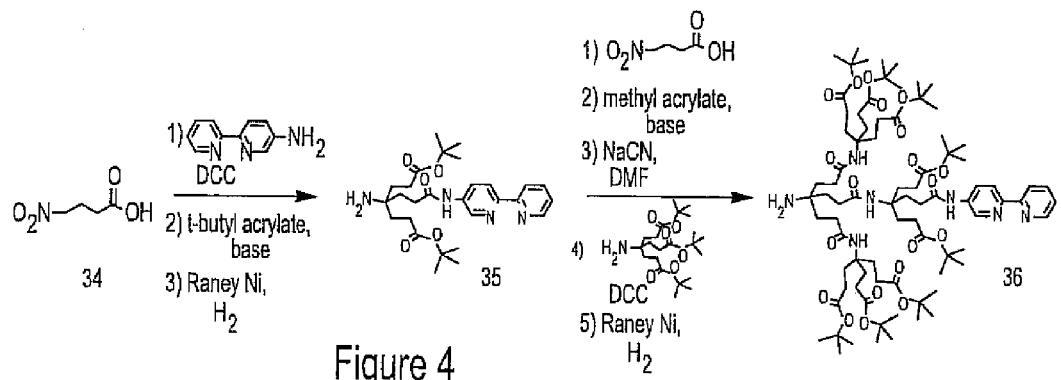
FIG. 4 shows the synthesis of a second generation bipyridyl-capped monomer.

As proof of the concept that branched architectures are dynamic with respect to functional group position, a dendrimer was constructed with a single ligating moiety bound to the surface of each quadrant of a dendrimer prepared using a tetravalent core. The key monomer 36 possessing a single bipyridine unit can be accessed via standard reactions (FIG. 4). Starting with 4-nitrobutyric acid (34), the bipyridyl diester 35 can be afforded by coupling of the aminobipyridine unit (Newkome et al., *J. Org. Chem.* 1997) followed by Michael-type addition of tert-butyl acrylate and nitro moiety reduction. (Dominguez et al., 1961) Amine acylation of 35 (DCC) addition of methyl acrylate, methyl ester deprotection (Mc-Murray, J., 1976) (NaCN, DMF), and coupling (DCC) of the aminotriester precursor to 6 with subsequent reduction of the nitro group to an amine (Weis et al., 1995) affords the desired homologated aminobipyridine 36. Acylation of four equivalents of 36 with tetraacyl chloride 37 yields dendrimer 38 (FIG. 5; the fourth bipyridine is not depicted), whereupon metal addition (Issberner et al., 1997) (e.g. $RuCl_3$, under reducing conditions) in dilute solution the trisbipyridine metal complex [e.g., Ru(II)]39 is expected. Other ligating species can be envisioned to function analogously, such as the siderophore-based dihydroxybenzene. (Tor et al., 1987) Standard analyses using UV, NMR, and mass spectrometry techniques are expected to confirm the presence of one free bipyridine and three complexed ligands. The structural proof-of-concept, for the Rubik's sphere model, (Tor et al., 1987) although synthetically lengthy, is critical to the demonstration that randomly placed functionalities on a dendron, sphere, or surface can contact, influence, or affect each other. The "Rubik's sphere concept has far reaching ramifications related to the incorporation of dendritic monomers that can rotate to favorable orientations to stabilize metals, clusters, and composites.

In view of the above, the present invention provides a monomer useful in the construction of dendrimers for investigating macromolecular torsional behavior. Such torsional behavior of branch architectures which are capable of being dynamic with respect to functional positioning groups. Such rotatable dendritic monomers capable of stabilizing metals, clusters and composites are used as "switches" for transferring ions or controlling ion transfer. Control can be obtained by the use of changing environments wherein the environment itself, whether hydrophobic and hydrophilic, high ionicity, low ioninicity, etc. can induce torsional changes which result in bringing ions or the like into or out of proximity with each other thereby able to either transfer or not transfer ionic moieties. Hence, the present invention provides significant utility in the molecular or electronics field. Likewise, such "Rubick's" sphere capability is useful in electrodes and solid state electronics.

Figure 6:
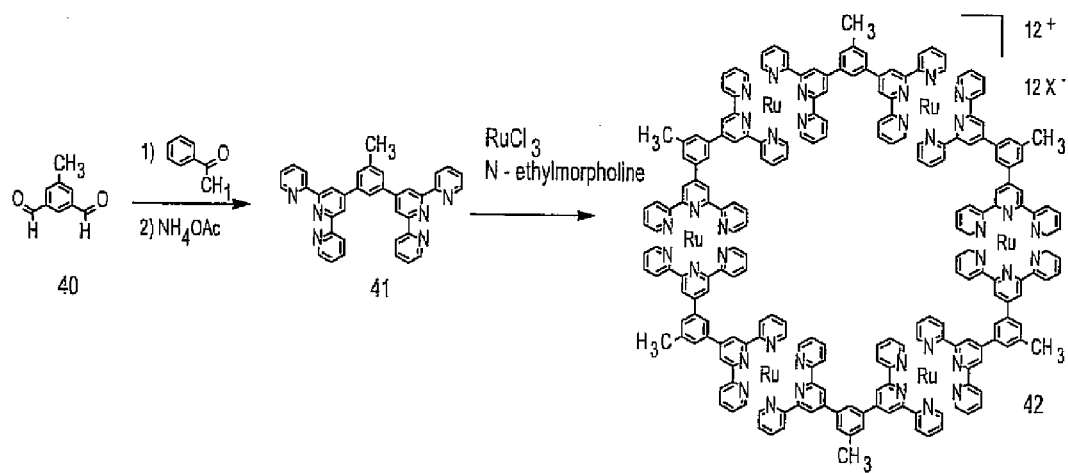
FIG. 6 shows the self-assembly synthesis of a hexa-Ru(II) cluster.

The present invention further provides means for making novel nanoscale metallomacrocycles. As part of efforts to develop nanoscale and molecular-sized energy storage devices, the potential self-assembly of polymetallic architectures for energy collection was investigated. These macrocycles are the first in a series of unique fractal polymers capable of molecular stacking and metal positioning. Synthesis of these novel materials is illustrated in FIG. 6 whereby a hexaruthenium ring is targeted. Beginning with the known dialdehyde 40 the primary bisterpyridine building block 41 was crafted via treatment with 2-acetylpyridine followed by reaction with $NH_4OAc$. Hexa-metallo ring 42 can then be accessed by a simple, one step, high yield, self-assembly of bisterpyridine 41 and six equivalents of $RuCl_3.Hn_2O$ in the presence of N-ethylmorpholine. Ruthenium connectivity was initially employed to prove the self-assembly process but other metals work in a comparable fashion. Also, rigid structural control facilitates the introduction of alternating metals. As well, 1,3,5- versus 2,4,6-external substituents can be incorporated, in a precise manner, affording a series of architecturally related materials.

Figure 7:
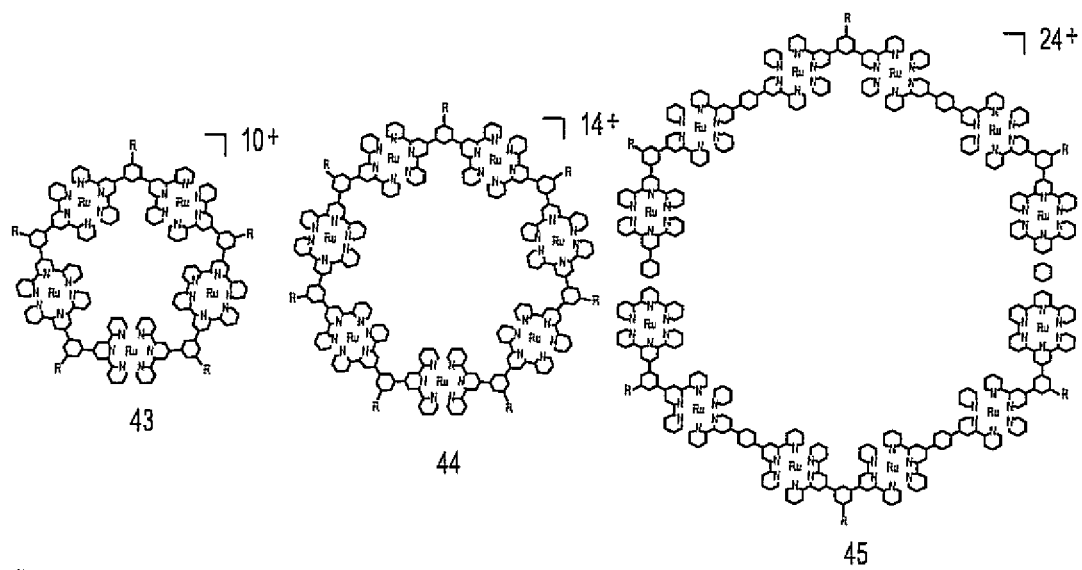
FIG. 7 shows structures for energy collection and storage made in accordance with the present invention.
Figure 7:
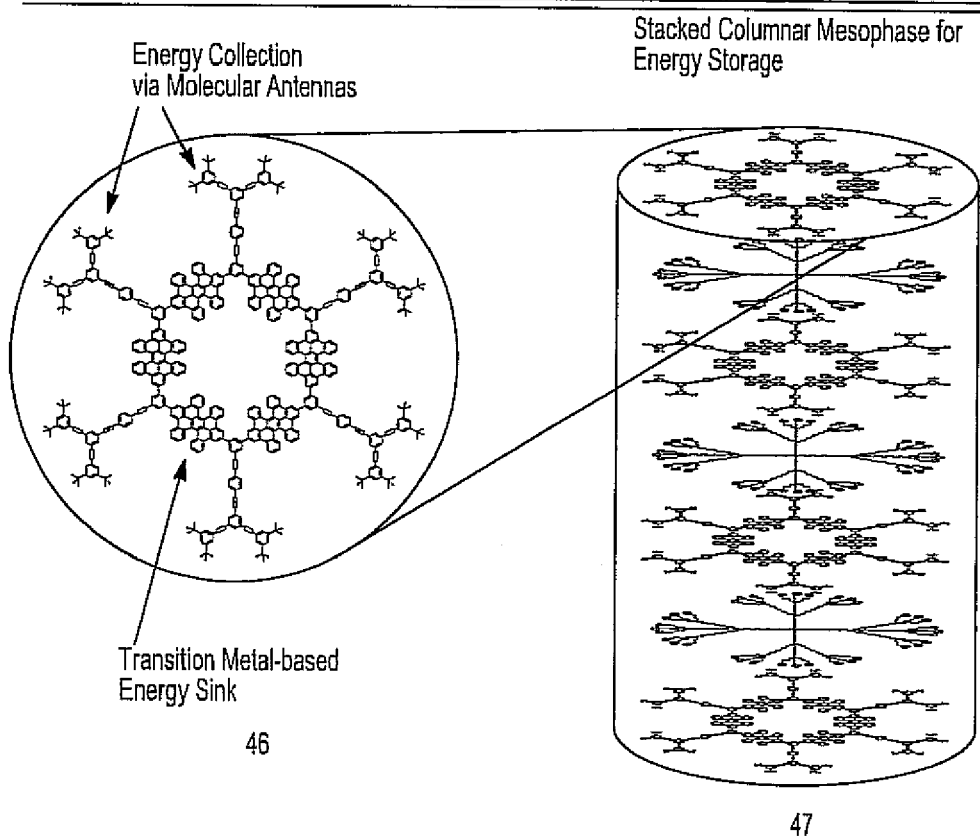

Different sized rings (43-45: FIG. 7) and derivatization of the peripheral methyl moieties via free radical halogenation (Newkome et al., *Synthesis*, 1984) and Susuki-type coupling (Xu et al., Stiff Dendritic Macromolecules: Extending Small Organic Chemistry to the Nonoscale Regime, *Polym. Prep.*, 1993; Xu et al., Synthesis and Characterization of a High Molecular Weight Stiff Dendrimer, *Angew. Chem., Int. Ed. Engl.*, 1993) of rigid or flexible appendages to facilitate "network" positioning of the poly-metal centers were investigated.

Figure 5:
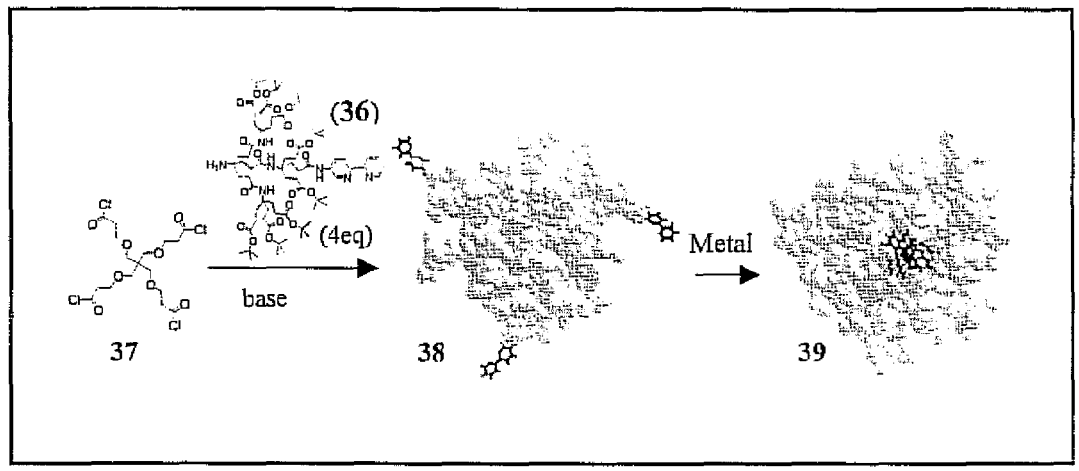
FIG. 5 shows the synthesis of a tetrabipyridine-terminated dendrimer for investigating macromolecular torsional behavior, the fourth, uncomplexed bipyridine not being shown.
Figure 8:
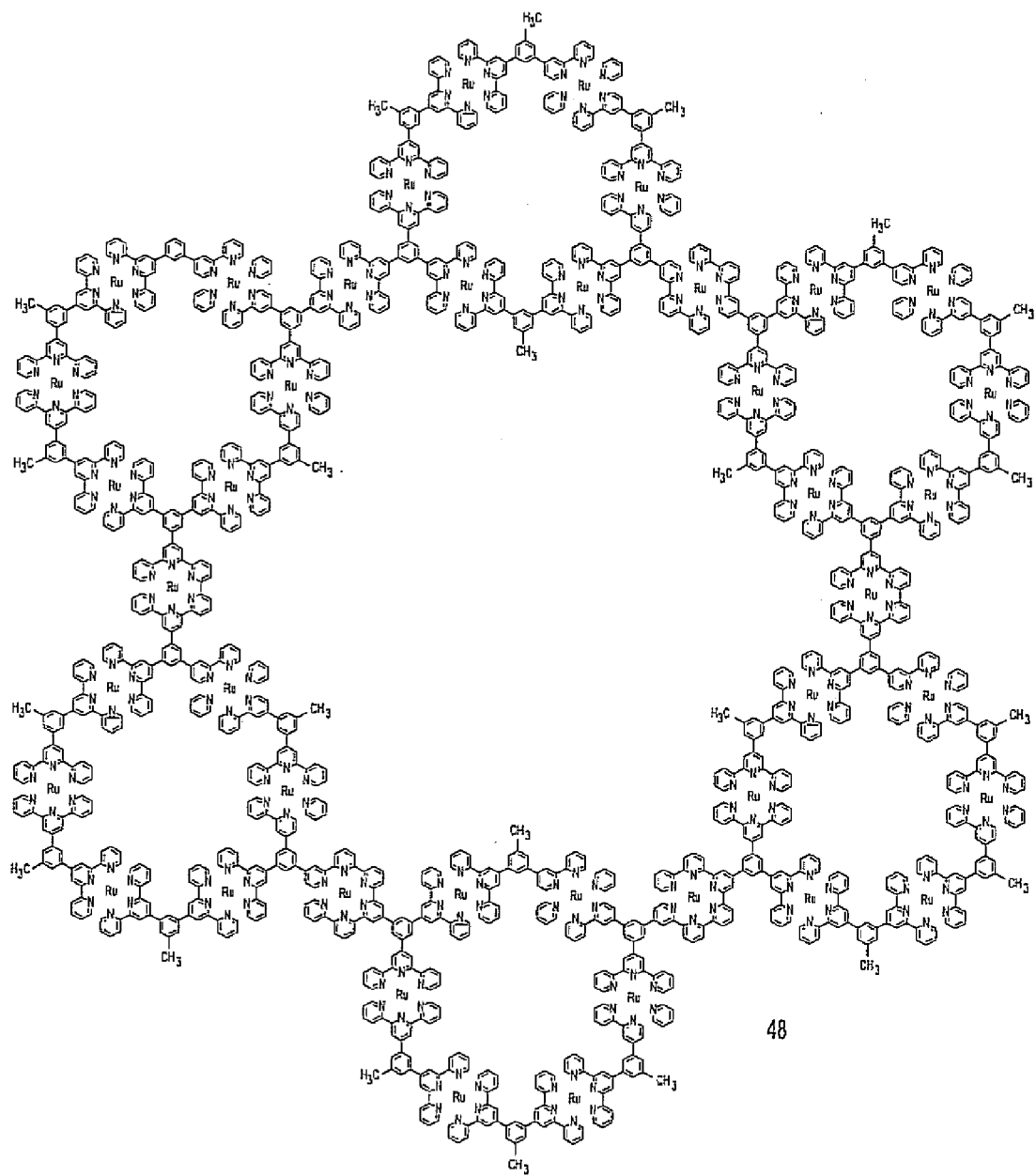
FIG. 8 shows a second generation fractal polymer made in accordance with the present invention.

For example, the branch modified structure 46, which is easily accessed via attachment of known, pre-formed polyphenylacetylene dendrons, (Xu et al., 1994) possesses structural requirements known to promote columnar mesophase (47) formation (Markovitsi et al., 1988) (i.e., near planarity and lipophilic arms positioned in a symmetrical cyclic array). Further, the phenylacetylene dendritic arms act as "molecular antennas," as reported in the literature, (Kopelman et al., 1998; Shortreed et al., 1997; Xu et al., 1994) for energy direction and concentration towards the electron-poor poly-metallic rings. Interestingly, stacked assemblies using anionic-terminated, hydrocarbon dendrimers as counter ions and "insulators" suggest their use in a number of areas of molecular electronics (i.e., LEDs, photodiodes, and thin film transistors) due to the potential to form alternating conducting and non-conducting layers. (Luryi et al., 1999; Krummenacker et al., 1995; Barnes et al., 1999) Although the first members of this series are depicted in FIG. 5, the creation of higher generations via the incorporation of additional terpyridine moieties can also be accomplished (48; FIG. 8).

In view of the above, the present invention provides compounds consisting of fractal-like, planar organometallic arrays. The term "fractal" is used in its accepted meaning, fractal geometry being concerned with the quantitative description of complex structures and the way in which the structures transform under a change of lens scales. The most simple fractals are self-similar or scale invariant structures that are invariant to an isotropic change of length scales. That is, they "look the same" under different magnifications. Familiar examples of such fractals are coastlines, clouds, and biological structures, such as the vascular system and nerve cells. During the past few years, these ideas have become widely disseminated and apply to a very broad range of materials and phenomena.

The fractals of the present invention provide for stackable, planar organometallic arrays, especially in higher generations of the fractals, capable of encapsulating, entraining, and stabilizing metal and non-metal nanoclusters for use as stacked electrode materials.

The fractals, as well as the previously disclosed dendrimers can be utilized in combination with various metals having the appropriate ionic properties for use in energy collection and storage devices. Examples of such metals, are Cu, Fe, Ru, Os, Zn, Co, Ni, Mn, Pd, Pt, Rh, Re, W, Ir, Au, and Ag.

Use of dendritic chemistry for the creation of new and improved anode and cathode materials is provided herein. Both "lithium"- and "lithium-rocking-chair"-type electrodes are targeted. Dendritic "void volume" employed in concert with internal and external metal or non-metal coordination sites as well as aqueous and non-aqueous chemical equilibria provide a wide range of option's for their construction.

Essentially, the unique, branched architecture of dendrimers simply provide a molecular-sized reaction vessel for component polymerization or colloidal stabilization and solubilization. Polymerization and particle stabilization using micelles and vesicles are well known. (Fendler et al., 1975; Fendler et al., 1994) Metal coordination to the interior of dendritic framework has been demonstrated in labs employing alkyne, (Newkome et al., Unimolecular micelles, *Angew. Chem., Int. Ed. Eng.,* 1991; Newkome at al., Alkane Cascade Polymers Possessing Micellar Topology: Micellanoic Acid Derivatives, *Angew. Chem., Int. Ed. Engl.,* 1991; Newkome et al., Chemistry within a Unimolecular Micelle Precursor: Boron Superclusters by Site- and Depth Specific Transformations of Dendrimers, *Angew. Chem.,* 1994; Newkome et al., Chemistry Within a Unimolecular Micelle Precursor Boron Superclusters by Site- and Depth-Specific Transformations of Dendrimers, *Angew. Chem., Int. Ed. Engl.,* 1994) bipyridine, (Newkome at al., Synthesis of Unsymmetrical 5,5'-Disubstituted 2,2'-Bipyridines, *J. Org. Chem.,* 1997; Newkome at al., Cascade Infrastructure Modification Via Integration of Application-Based Monomers, *Polym. Mater. Sci. Eng.,* 1995; Newkome et al., Design, Syntheses, Complexation, and Electrochemistry of Polynuclear Metallodendrimers Possessing Internal Metal Binding Loci, *Chem. Eur. J.,* 1999) and terpyridine moeities, (Newkome et al., Electroactive Metallomacromolecules via Tetrabis(2,2':6'2"-Terpyridine)ruthenium(II) Complexes: Dendritic Networks towards Constitutional Isomers and Neutral Species without External Counterions, *Chem. Commun.,* 1998; Newkome et al., Neutral highly branched metallomacromolecules: Incorporation of (2,2':6'2"-terpyridine)ruthenium(II) complex without external counterions, *Chem. Commun.,* 1999; Newkome et al., Construction of Dendritic Assemblies: A Tailored Approach to Isomeric Metallomacromolecules by Means of Bis(2,2':6'2"-terpyridine)ruthenium(II) Connectivity, *Macromolecules,* 1998) while coordination and subsequent reaction have produced "nanoparticles" (i.e., zero valent Pt clusters [Zhao et al., Dendrimer-Encapsulated Pt Nanoparticles: Synthesis, Characterization, and Applications to Catalysis, *Adv. Mater. (Weinhem, Fed. Repub. Ger.),* 1999; Chechik et al., 1999; Zhao et al., Homogeneous Hydrogenation Catalysis with Monodisperse, Dendrimer-Encapsulated Pd and Pt Nanoparticles, *Angew. Chem. Int. Ed.,* 1999] and $CuS_2$ [Balogh et al., 1998; Tan at al., 1999; Dagani, R., 1999]).

Figure 9:
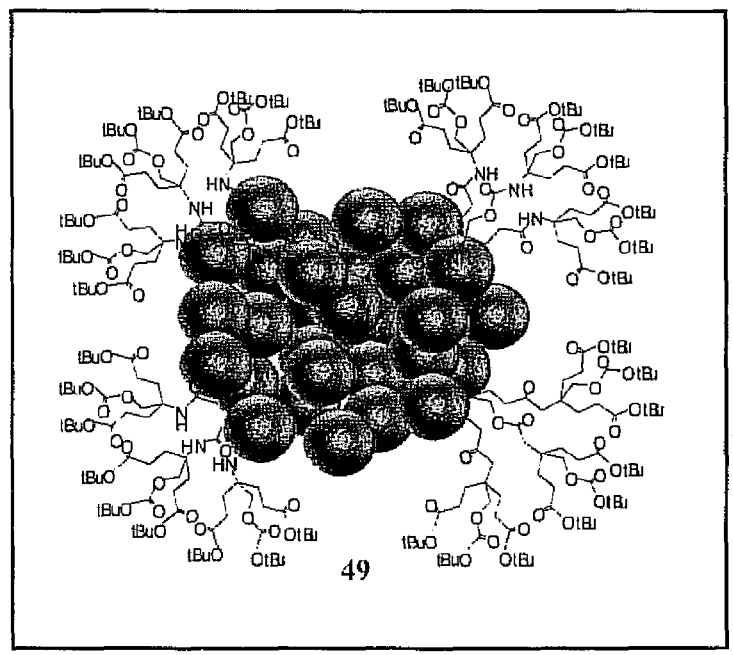
FIG. 9 shows a dendritic nano-cluster templating and stabilization made in accordance with the present invention.

Dendrimers can be used as templates (49; FIG. 9) for the preparation of uniform, nanocrystallite materials such as hydrous $RuO_2$, is (Ru—Ti) $O_x$ (Kriesel et al., 1999; Long et al., 1999) and organic-based binary material such as polyethyleneoxide-dihydrophenazine block copolymer. (Tran at al., 1998) Use of dendrimers for construction of nonocrystallites for electrode materials allows for high surface area and near uniform dimensions thereby enhancing electrode stability, conductivity, and capacity. The concept of dendrimer nanocrystallite formation is predicated on the preparation of semiconductor crystallites via "arrested precipitation" techniques, or templated polymerization, using structured reaction media such as zeolites, ionomers, porous glass, vesicles, micelles, and gels. (Steigerwald at al., 1990) More recently, CdS clusters have been derivatized with pyridine units and fabricated into superarrays, (Steigerwald, et al., Semiconductor Crystallites: A Clas of Large Molecules, *Acc. Chem. Res.,* 1990) and superlattices, (Que et al., 1988; Que at al., 1990) thus electronically coupling the individual clusters for enhanced luminescence emission properties. Thus, use of the "void volume" inherent in dendritic assemblies and components affords an ideal method for preparation of crystallites with a high degree of purity and monodispersity, as well as at sizes relevant to the "quantum effect" (i.e., 50 Å or less). (Que et al., 1988; Que et al., 1990; Weller, H., 1993)

In view of the above, the present invention most generally provides a dendrimer nanocrystallite.

The present invention further provides a method of preparing polyterpyridyl ligands in a self-assembling manner. By "self-assembling" it is meant that the combination of the components will, without further chemical or physical prompting assemble into a higher order (fractal) architecture.

More specifically, the present invention provides a preparation of a bis(terpyridine) monomer possessing a 120° concave angle with respect to the two ligating moieties. This would facilitate the assembly of six building blocks with six connecting metals in the ubiquitous benzenoid architecture. The potential to synthesize such constructs, with little equilibration (metal-ligand exchange) under mild physiochemical conditions, is predicated on the unique strength of the terpyridine-Ru coordination.

Figure 10:
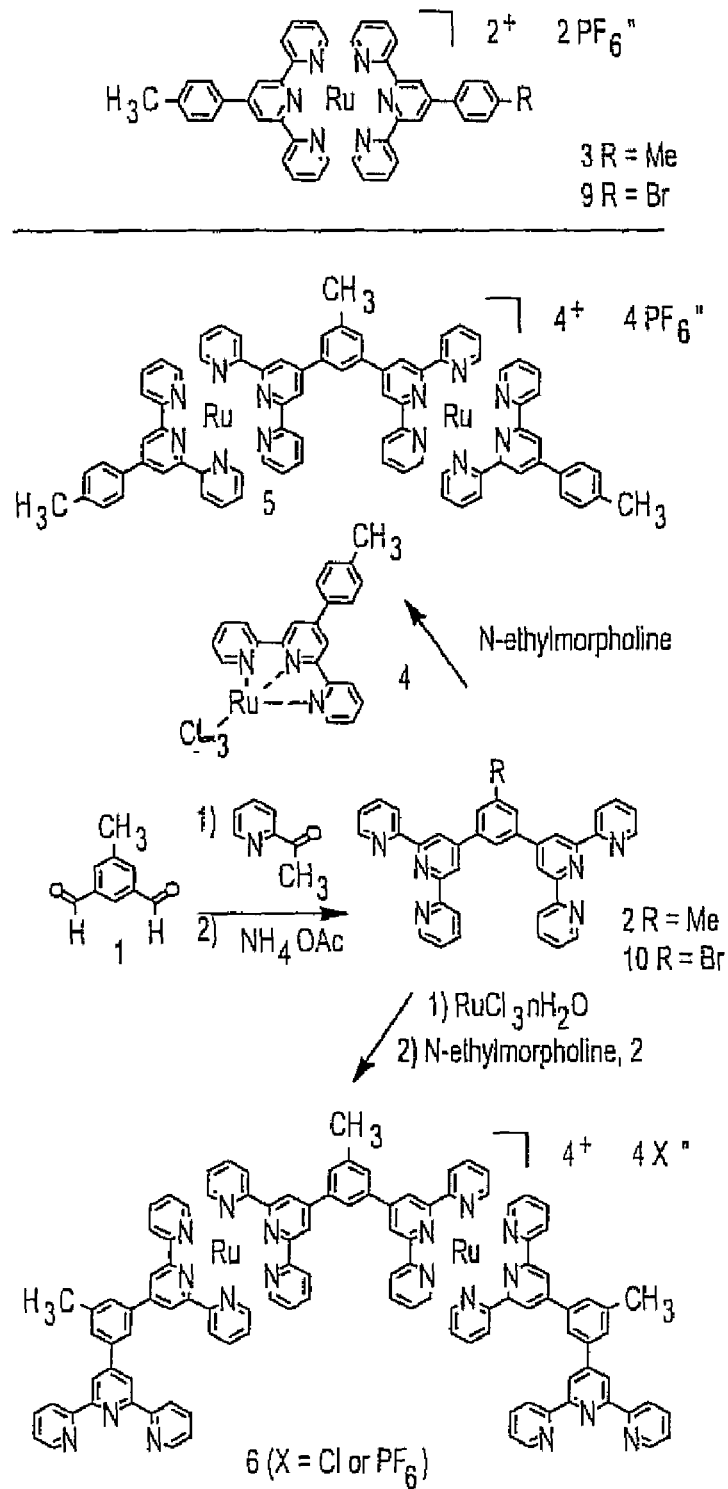
FIG. 10 shows the synthesis of the key monomer and primer for macro cycle construction in accordance with the present invention.
Figure 11:
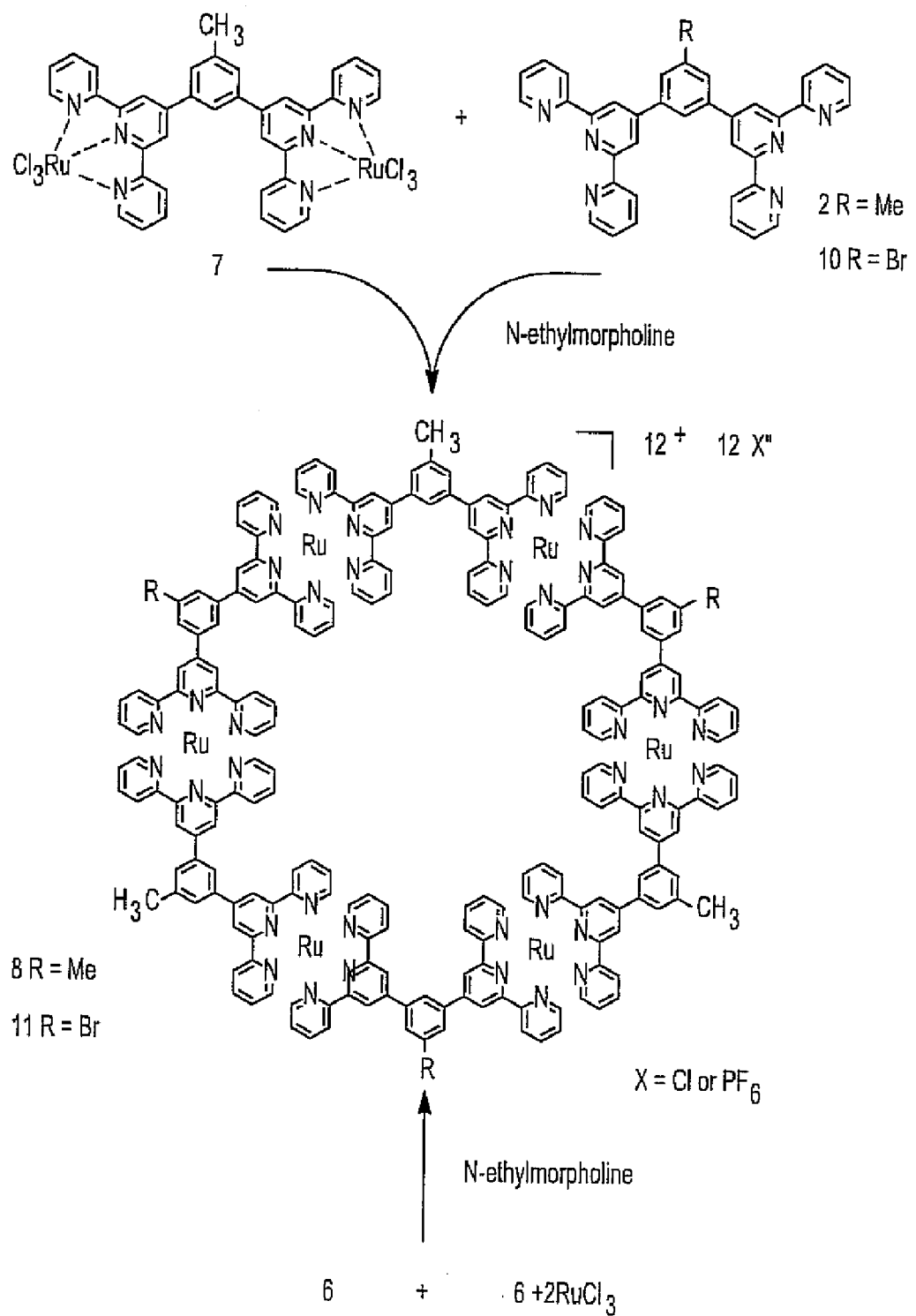
FIG. 11 shows the self- and directed-synthesis of macro cycles in accordance with the present invention.

Synthesis of the requisite building block began via treatment of the known dialdehyde (28) 1 (FIG. 9) with ecess 2-acetylpyridine (29) followed by $NH_4Oac$ to afford (66%) of the desired angular (120°) bis(terpyridine) 2. Confirmation of this structure included $^1H$ NMR absorptions at 7.38 (dd; 5,5"), 7.82 (s; 4,6 Ar), and 8.83 ppm (s; 3', 5') Reaction of hexagonal precursor 2 with two equivalents of $RuCl_3$-$nH_2O$ produced the minimally soluble, paramagnetic bis[Ru(III)] adduct 7 (FIG. 10) which was treated without further purification with one equivalent of monomer 2 under reducing conditions (N-ethylmorpholine) to yield (85%) the self-assembled, diamagnetic, hexameric Ru(II) complex 8 (Table 1). The $^1H$ NMR spectrum (FIG. 11) of the purified material revealed a single absorption at 2.90 ppm ($CH_3$) suggesting the presence of only one type of monomeric unit in contrast to that expected for a linear oligomer. Other diagnostic spectral attributes ('H NMR) included upfield and downfield shifts, respectively, of the 6,6" signals ($\delta$ 7.62; $\Delta\delta$1.13) and the 3',5' signals ($\delta$ 9.37; $\Delta\delta$ 0.54). COSY and HETCOR spectra of the bis(ligand) and the self-assembled macrocycle verified the peak assignments and coupling patterns. Hexamer 8, isolated as the 12 Cl' salt, exhibited solubility in MeOH and hot $H_2O$ while conversion to the 12 $PF_6^-$ facilitated solubilization in acetonitrile, acetone, and dimethylsulfoxide.

In order to ensure structural verification of macrocycle 8, a stepwise, directed route to the material was devised. Initially, further characterization of the key monomer 2, as well as the bis(terpyridyl)-Ru(II) connective moieties, was provided by the formation of the mono- and di-Ru(II) complexes 3 and 5 (FIG. 9). Reaction of 4'-(4-methylphenyl)-2,2':6',2"-terpyridine (30) with $RuCl_3$-$nH_2O$ followed by addition of the unmetallated mono- and di-terpyridine ligands (4 and 2, respectively) afforded the desired complexes. As in the case of hexamer 8, constructs 3 and 5 exhibited a downfield shift ($^1$H NMR) of the 3',5' proton resonances ($\delta$ 9.20; $\Delta\delta$ 0.46) and an upfield shift of the 6,6" signals ($\delta$7.62; $\Delta\delta$ 1.07). Bis(Ru) complex 5 was also prepared employing ligand 7 followed by capping with the free monoterpyridine precursor to 4.

Subsequently, the diamagnetic tris(oligomer) 6 was prepared from building block 2 via sequential treatment with two equivalents of $RuCl_3$-$nH_2O$ and then unmetallated monomer 2. The $^1$H NMR spectrum of trimer 6 showed a complex pattern of broadened absorptions in the aromatic region ($\delta$ 9.76-7.40) as well as the two anticipated singlets arising from the non-equivalent methyl groups ($\delta$ 2.79, 3H, 2.94, 6H). Finally, reaction of the oligomer 6 with one equivalent of its bis[terminal Ru(III)] adduct yielded a material possessing identical spectral and physical characteristics to that of the self-assembled hexamer 8. Notablyu, a silica TLC of the macrocycle 8, eluting with a mixture of $CH_3CN$ and aqueous $KNO_3$, clearly showed the absence of any starting materials, while the UV spectrum extinction coefficients ($\epsilon$) exhibited a 5.1, 5.5, and 5.8 fold increase for $\lambda_{max}$ at 290, 312 and 496 nm, respectively (Table 2), when compared to analogous measured coefficients for the monoRu(II) complex 3.

Figure 12:
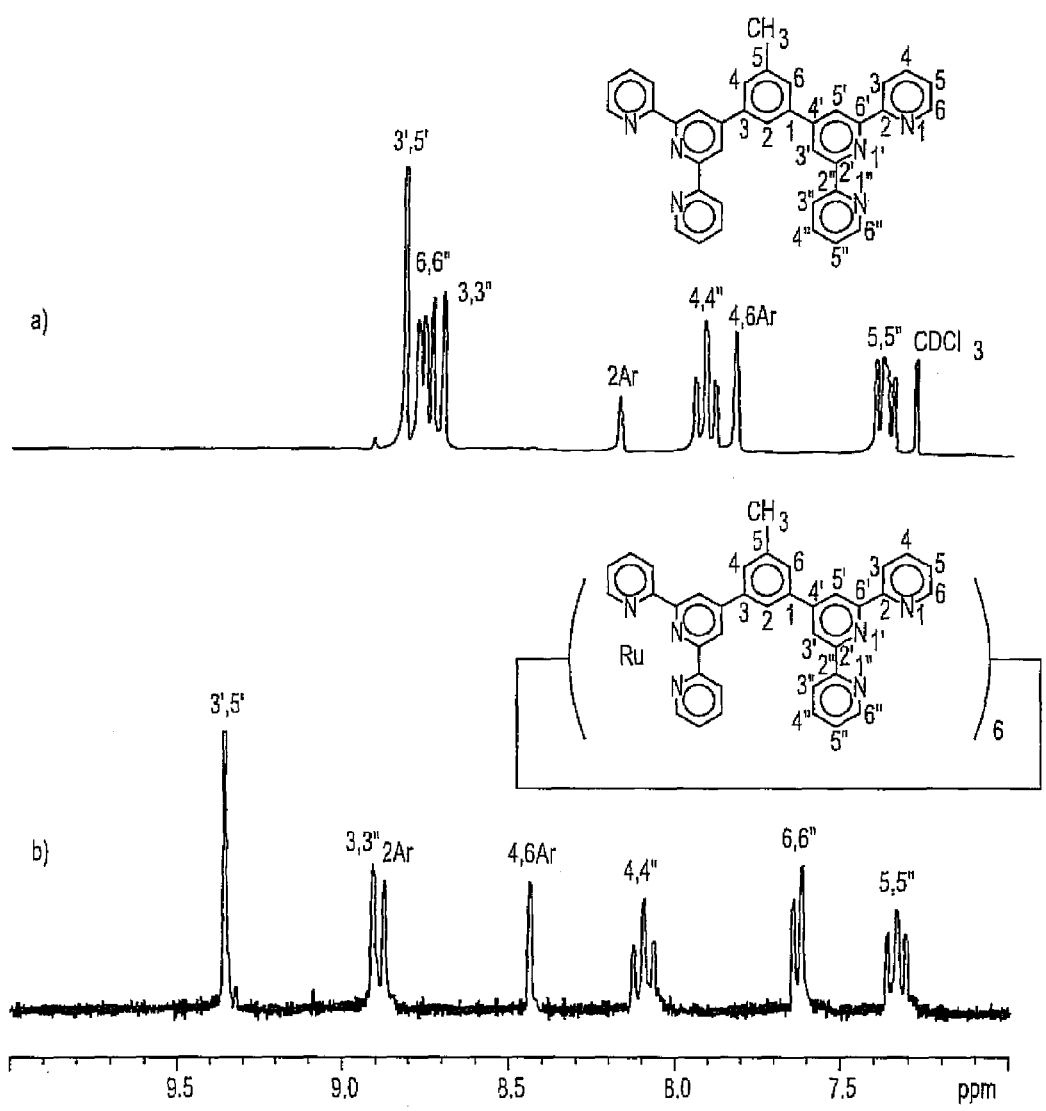
FIG. 12 shows the $^1$H NMR spectra of the bis(terpyridine) ligand and self assembled hexaRu(II) complex made in accordance with the present invention.
Figure 12A:
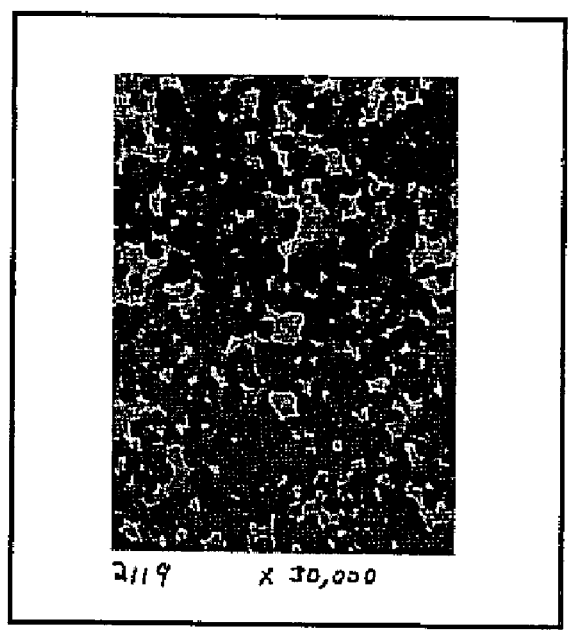
FIG. 12A shows an electron micrograph of a regularly shaped aggregate.
Figure 12B:
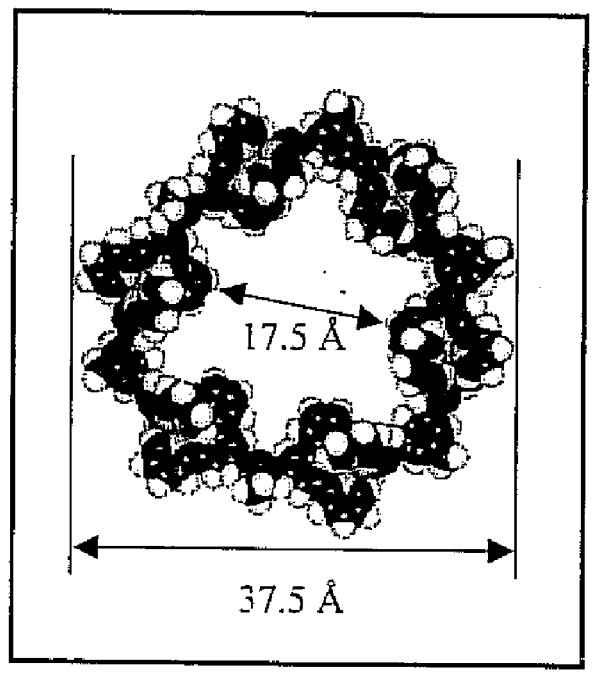
FIG. 12B shows a computer generated cpk model of a macro cycle made in accordance with the present invention.

An electron micrograph (EM) of $8^{+12}$ (12 $PF_6$) revealed a regular, packing morphology with particle sizes ranging from $\equiv$160 to 350 Å (FIG. 12a) while powder X-ray diffraction showed only short-range order with determined d-spacings at 7.99, 6.24, and 4.32 Å. Powder diffraction spectra of bis[Ru (II)] complex 5 exhibited a similar pattern (d-spacings; 10.11, 7.58, 5.80 and 4.32 Å). Molecular modeling of macrocycle 8 (FIG. 12b) indicated a diameter of 37.5 Å, a minimum inner void distance of 17.5 Å and a distance between adjacent Ru metals of 13.5 Å.

In an effort to modify the generally poor solubility of macrocycle 8, as well as provide organizational scaffolding for non-bonded network formation, the counter ions in $8^{+12}$ (12 Cl) were exchanged with a dodecarboxylate-terminated dendrimer (31) to give $8^{+12}[C(CH_2OCH_2CH_2CONHC(CH_2CH_2CO_2^-)_3)_4]$, which is an extremely insoluble assembly. However, a 1:1 mixture of hexamer 8 and a third generation carboxylate-terminated dendrimer gave $8^{+12}$ (G3-108-$CO_2^-$), which produced a deep red $D_2O$ solution (25° C.) allowing verification of aqueous solubility via $^1$H NMR. The use of compact, charge concentrated, (psuedo)spherical dendrimers possessing uniquely positioned anionic counterion character affords a convenient circumvention of the spacial randomness of traditional simple counterions in such complexes.

These results have led to the construction of heteroleptic macrocycles. Bromo analogs of monomethyl terpyridine 2 and the p-methyl monoterpyridine 4 were prepared starting with 5-bromo-m-xylene or 4-bromobenzaldehyde, respectively. Reaction of the bromomonoterpyridyl ligand (not depicted) with Ru(III) adduct 4 gave the anticipated Ru(II) complex 9 exhibiting nearly identical $^1$H and $^{13}$C NMR spectra to that of complex 3. While addition of the bromo building block 10 to the bis[Ru(III)] adduct 7 afforded the mixed monomer macrocycle 11. Evidence for its formation includes a symmetrically similar yet expectedly broadened $^1$H NMR spectrum corresponding exactly to that of the hexamethyl analog 8. HETCOR experiments further support the structure.

In conclusion, the iterative synthetic method combined with fundamental properties of branched macromolecular architecture allows the realization of new materials to promote advances in energy storage devices and their components. Construction of a modular set of building blocks or monomers is essential and key to the realization of the chemistry discussed herein.

Dendrimer-based electrolyte materials enhance solid state lithium-type batteries via improvements in such properties as electrode separation, electrolyte solubility, and ion conduction, and safety. Operational temperature ranges increase due to better electrolyte solubility and matrix stability.

Improved anode and cathode materials to result via the potential for branched architectures to be employed for the preparation and stabilization of metal and non-metal colloids and composites. Use branched architectures for binders in existing materials improve surface areas and retard polarization gradients thereby enhancing ion diffusion and overall conduction.

Metal encapsulation with branched architectures finds utility in many areas of battery technology and molecular electronics. Ramifications include the ability to produce smaller particles with greater cumulative surface areas that ultimately facilitate better ion diffusion within the electrode and at the electrode-electrolyte interface. Use of dendritic vessels as molecular reactors, in a similar fashion as micelles are employed for polymerizations, allow the investigation of new organic- and organometallic-based copolymers and composites.

The single-step construction of new fractal-like, planar organometallic arrays provides new methods of energy storage and conduction via the potential to precisely position metals within large networks. Combinatorial methods of macromolecular construction are proposed that ultimately lead to the creation of single molecules possessing the capability of energy storage and release (i.e., molecular batteries). Creation of molecules with the capacity to take advantage of multiple environmental interactions at multiple sites within the superstructure provides vast opportunity for the examination and evaluation of materials related to energy storage devices.

The overall unifying theme presented in this proposal relates to the melding of iterative synthetic protocols with more mature research arenas for the production of utilitarian materials. Ultimate control of macromolecular structural features leads to ultimate control of macromolecular properties and thereby lead to tunable macroscopic material properties.

Throughout this application, various publications, including United States patents, are referenced by author and year and patents by number. Full citations for the publications are listed below. The disclosures of these publications and patents in their entireties are hereby incorporated by reference into this application in order to more fully describe the state of the art to which this invention pertains.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the described invention, the invention may be practiced otherwise than as specifically described.

REFERENCES

Burke and Olson, "Preparation of Clone Libraries in Yeast Artificial-Chromosome Vectors" in *Methods in Enzymology*, Vol. 194, "Guide to Yeast Genetics and Molecular Biology", eds. C. Guthrie and G. Fink, Academic Press, Inc., Chap. 17, pp. 251-270 (1991).

Capecchi, "Altering the genome by homologous recombination" *Science* 244:1288-1292 (1989).

Davies et al., "Targeted alterations in yeast artificial chromosomes for inter-species gene transfer", *Nucleic Acids Research*, Vol. 20, No. 11, pp. 2693-2698 (1992).

Dickinson at al., "High frequency gene targeting using insertional vectors", *Human Molecular Genetics*, Vol. 2, No. 8, pp. 1299-1302 (1993).

Duff and Lincoln, "Insertion of a pathogenic mutation into a yeast artificial chromosome containing the human APP gene and expression in ES cells", *Research Advances in Alzheimer's Disease and Related Disorders*, 1995.

Huxley et al., "The human HPRT gene on a yeast artificial chromosome is functional when transferred to mouse cells by cell fusion", *Genomics*, 9:742-750 (1991).

Jakobovits et al., "Germ-line transmission and expression of a human-derived yeast artificial chromosome", *Nature*, Vol. 362, pp. 255-261 (1993).

Lamb et al., "Introduction and expression of the 400 kilobase precursor amyloid protein gene in transgenic mice", *Nature Genetics, Vol.* 5, pp. 22-29 (1993).

Pearson and Choi, *Expression of the human b-amyloid precursor protein gene from a heast artificial chromosome in transgenic mice*. Proc. Natl. Scad. Sci. USA, 1993. 90:10578-82.

Rothstein, "Targeting, disruption, replacement, and allele rescue: integrative DNA transformation in yeast" in *Methods in Enzymology*, Vol. 194, "Guide to Yeast Genetics and Molecular Biology", eds. C. Guthrie and G. Fink, Academic Press, Inc., Chap. 19, pp. 281-301 (1991).

Schedl at al., "A yeast artificial chromosome covering the tyrosinase gene confers copy number-dependent expression in transgenic mice", *Nature, Vol.* 362, pp. 258-261 (1993).

Strauss et al., "Germ line transmission of a yeast artificial chromosome spanning the murine $a_1$ (I) collagen locus", *Science*, Vol. 259, pp. 1904-1907 (1993).

Gilboa, E, Eglitis, M A, Kantoff, P W, Anderson, W F: Transfer and expression of cloned genes using retroviral vectors. BioTechniques 4(6):504-512, 1986.

Cregg J M, Vedvick T S, Raschke W C: Recent Advances in the Expression of Foreign Genes in *Pichia pastoris*, Bio/Technology 11:905-910, 1993

Culver, 1998. Site-Directed recombination for repair of mutations in the human ADA gene. (Abstract) Antisense DNA & RNA based therapeutics, February, 1998, Coronado, Calif.

Huston et al, 1991 "Protein engineering of single-chain Fv analogs and fusion proteins" in Methods in Enzymology (J J Langone, ed.; Academic Press, New York, N.Y.) 203:46-88.

Johnson and Bird, 1991 "Construction of single-chain Fvb derivatives of monoclonal antibodies and their production in *Escherichia coli* in Methods in Enzymology (J J Langone, ed.; Academic Press, New York, N.Y.) 203:88-99.

Mernaugh and Mernaugh, 1995 "An overview of phage-displayed recombinant antibodies" in Molecular Methods In Plant Pathology (RP Singh and US Singh, eds.; CRC Press Inc., Boca Raton, Fla.) pp. 359-365.

Newkome, G. R.; Moorefield, C. N.; Vogtle, F. Dendritic Molecules: Concepts, Syntheses, Perspective; VCH: Weinheim, Germany, 1996.

Hult, A.; Johansson, M.; Malmstrom, E. "Hyperbranched Polymers" In Advances in Polymer Science: Branched Polymers; Springer-Verlag: Berlin, Heidelberg, New York, 1999; Chapter 1, pp. 2-34.

Roovers, J.; Comanita, B. "Dendrimers and Dendrimer-Polymer Hybrids". In Advanced in Polymer Science: Branched Polymers; Springer-Verlag: Berlin, Heidelberg, New York, 1999, pp. 180-228.

Young, J. K.; Baker, G. R.; Newkome, G. R.; Morris, K. F.; Johnson, C. S., Jr. "Smart" Cascade Polymers. Modular Syntheses of Four-Directional Dendritic Macromolecules with Acidic, Neutral, or Basic Terminal Groups and the Effect of pH Changes on Their Hydrodynamic Radii." Macromolecules 1994, 27 (13), 3464-3471.

Newkome, G. R.; Weis, C. D.; Moorefield, C. N.; Baker, G. R.; Childs, B. J.; Epperson, J. "Isocyanata-Based Dendritic Building Blocks: Combinatorial Tier Construction and Macromolecular Property Modification.: Angew. Chem., Int. Ed. Engl. 1998, 37, 307-310.

Lipkowski, J.; Ross, P. N. Electrochemistry of Novel Materials; VCH: New York, N.Y., 1994; p. Chapters 2 and 3.

Owen, J. R. "Rechargable lithium batteries". Chem. Soc. Rev. 1997, 26, 259-267.

Newkome, G. R.; He, E. "Nanometric dendritic macromolecules: stepwise assembly by double (2,2':6',2''-terpyridine) ruthenium(II) connectivity." J. Mater. Chem. 1997, 7(7), 1237-1244.

Newkome, G. R.; He, E.; Godinez, L. A.; Baker, G. R. "Electroactive Metallomacromolecules via Tetrabis(2,2':6',2''-Terpyridine)ruthenium(II) Complexes: Dendritic Networks towards Constitutional Isomers and Neutral Species without External Counterions." Chem. Commun. 1998, 27-28.

Newkome, G. R.; Lin, X.; Young, J. K. "Syntheses of Amine Building Blocks for Dendritic Macromolecule Construction." Synlett 1992, (1), 53-54.

Newkome, G. R.; He, E.; Godinez, L. A.; Baker, G. R. "Neutral highly branches metallomacromolecules: Incorporation of (2,2': 6', 2''-terpyridine)ruthenium(II) complex without external counterions." Chem. Commun. 1999, 27-28.

Narayanan, V. V.; Newkome, G. R.; Echegoyen, L.; Perez-Cordero, E. "Novel Dendrimers Possessing Internal Electroactive Quinoid Moieties." Polym. Prep. 1996, 37, 419-420.

Newkome, G. R.; Narayanan, V. V.; Godinez, L. A. "Anthraquinoid-based Extended Dendritic Monomers: Electrochemical Comparisons". Designed Monomers and Polymers 1999, submitted.

Newkome, G. R.; Narayanan, V. V.; Godinez, L. A.; Perez-Cordero, E.; Echegoyen, L. "A Tailored Approach to the Syntheses of Electroactive Dendrimers Based on Diaminoanthraquinones." Macromolecules 1999, in press.

Newkome, G. R.; Narayanan, V. V.; Echegoyen, L.; Perez-Cordero, E; Luftmann, H. "Synthesis and Chemistry of Novel Dendritic Macromolecules Possessing Internal Electroactive Anthraquinonoid Moieties." Macromolecules 1997, 30(17), 5187-5191.

Newkome, G. R. and Moorefield, C. N. "Unimolecular Micelles and Method of Making the Same". U.S. Pat. No. 5,154,853, 1992.

Newkome, G. R.; Moorefield, C. N.; Baker, G. R.; Saunders, M. J.; Grossman, S. H. "Unimolecular micelles". Angew. Chem. Int. Ed. Engl. 1991, 30(9), 1178-1180.

Newkome, G. R.; Weis, C. D.; Moorefield, C. N.; Fronczek, F. R. "A useful dendritic building block: di-tert-butyl 4-[2-tert-butoxycarbonyl)ethyl]-4-isocyanato-1,7-heptanedicarboxylate." Tetrahedron Lett. 1997, 38(40), 7053-7056.

Newkome, G. R.; Weis, C. D.; Childs, B. J. "Synthesis of 1→3 Branched isocyanate Monomers for Dendritic Construction." Designed Monomers and Polymers 1997, I(1) 3-14.

Newkome, G. R.; Childs, B. J.; Rourk, M. J.; Baker, G. R.; Moorefield, C. N. "Dendrimer Construction and Macromolecular Property Modification via Combinatorial Methods." J. Combinatorial Chem. 1999, in press.

Newkome, G. R. and Moorefield, C. N. "Combinatorial Method of Forming Cascade Polymer Surfaces." U.S. Pat. No. 5,886,126, 1999.

Newkome, G. R. and Moorefield, C. N. "Combinatorial Method of Forming Cascade Polymer Surfaces." U.S. Pat. No. 5,886,127, 1999.

Salomon, M. "Solubility problems relating to lithium battery electrolytes". Pure Appl. Chem. 1998, 70(10), 1905-1912.

Newkome, G. R.; Moorefield, C. N.; Baker, G. R.; Johnson, A. L.; Behera, R. K. "Alkane Cascade Polymers Possessing Micellar Topology: Micellanoic Acid Derivatives." Angew. Chem., Int. Ed. Engl. 1991, 30(9), 1176-1178.

Buckmann, A. F.; Morr, M. "Functionaiization of Polyethylene glycol) and Monomethoxy-Poly(ethylene glycol)." Makromol. Chem. 1981, 182, 1379-1384.

Burns, C. J.; Field, L. D.; Hashimoto, K.; Petteys, B. J.; Ridley, D. D.; Sandanayake, K. R. A. S. "A convenient synthetic route to differentially functionalized long chain polyethylene glycols." Synth. Commun. 1999, 29 (13), 2337-2347.

Cisak, A.; Werblan, L. High-energy Non-aqueous Batteries; Horwood: New York, 1993.

Newkome, G. R. and Weis, C. D. "Method of Utilizing Isocyanate Linkages for Forming Multi-Tier Cascade Polymers." U.S. Pat. No. 5,773,551, 1998.

Newkome, G. R.; Baker, G. R.; Behera, R. K.; Johnson, A. L.; Moorefield, C. N.; Weis, C. D.; Cao, W. J.; Young, J. K. "Cascade Molecules. 15. Synthesis of Tris(3-substituted) Tripropylnitromethanes." Synthesis 1991, (10), 839-841.

Zhang, J.; Moore, J. S.; Xu, Z.; Aguirre, R. A. "Nanoarchitectures. 1. Controlled synthesis of phenylacetylene sequences." J. Am. Chem. Soc. 1992, 114(6), 2273-2274.

Zhang, J.; Pesak, D. J.; Ludwick, J. L.; Moore, J. S. "Geometrically-controlled and site-specifically-functionalized phenylacetylene macrocycles." J. Am. Chem. Soc. 1994, 116(10), 4227-4239.

Newkome, G. R.; Gross, J.; Patri, A. K. "Synthesis of Unsymmetrical 5,5'-Disubstituted 2,2'-Bipyridines.: J. Org. Chem. 1997, 62(9), 3013-3014.

Dominguez, X. A.; Lopez, I. C.; Franco, R. "Simple Preparation of a Very Active Raney Nickel Catalyst." J. Org. Chem. 1961, 26(5), 1625.

McMurry, J. "Ester Cleavages Via $S_N2$-Type Dealkylation." In Organic Reactions; Wiley: New York, N.Y., 1976; Chapter 2, pp. 187-224.

Weis, C. D.; Newkome, G. R. "Reduction of Nitro Substituted Tertiary Alkanes", Synthesis 1995 (9) 1053-1065.

Issberner, J.; Vogtle, F.; De Cola, L.; Baizani, V. "Dendritic Bipyridine Ligands and Their Tris(Bipyridine)ruthenium (II) Chelates-Syntheses, Absorption Spectra, and Photophysical Properties." Chem. Eur. J. 1997, 3 (5), 706-712.

Tor, Y.; Libman, J.; Shanzer, A.; Lifson, S. "Biomimetric Ferric Ion Carriers. A Chiral Analogue of Enterobactin.: J. Am. Chem. Soc. 1987, 109(21), 6517-6518.

Tor, Y.; Libman, J.; Shanzer, A.; Lifson, S. "Biomimetic Ferric Ion Carriers. A Chiral Analogue of Enterobactin.: J. Am. Chem. Soc. 1987, 109(21), 6517-6518.

Tor, Y.; Libman, J.; Shanzer, A. "Biomimetic Ferric Ion Carriers. Chiral Ferrichrome Analogues.: J. Am. Chem. Soc. 1987, 109(21), 6518-6519.

Newkome, G. R.; Kiefer, G. E.; Xia, Y.-J.; Gupta, V. K. "α-Methyl Functionalization of Electron-Poor Heterocycles: Free Radical Chlorination." Synthesis 1984, 676-679.

Xu, Z.; Moore, J. S. "Stiff Dendritic Macromolecules: Extending Small Organic Chemistry to the Nanoscale Regime." Polym. Prep. 1993, 34, 128-129.

Xu, Z.; Moore, J. S. "Synthesis and Characterization of a High Molecular Weight Stiff Dendrimer." Angew. Chem. Int. Ed. Engl. 1993, 32(2), 246-248.

Xu, Z.; Kyan, B.; Moore, J. S. "Stiff Dendritic Macromolecules Based on Phenylacetylenes." In Advances in Dendritic Macromolecules; G. R. Newkome, ed., JAI: Greenwich, Conn., 1994; Chapter 2, pp. 69-104.

Markovitsi, D.; Tran-Thi, T.-H.; Briois, V.; Simon, J.; Ohta, K. "Laser Induced Triplet Excitons in the Columnar Phases of an Octasubstituted Metal Free Phthalocyanine." J. Am. Chem. Soc. 1988, 110(6), 2001-2002.

Kopelman, R.; Shortreed, M.; Shi, Z.-Y.; Tan, W.; Xu, Z.; Moore, J. S.; Bar-Haim, A.; Kieffer, J. "Spectroscopic Evidence for Excitonic Localization in Fractal Antenna Supermolecules." Phys. Rev. Lett. 1998, 78(7), 1239-1242.

Shortreed, M. R.; Swallen, S. F.; Shi, Z.-Y.; Tan, W.; Xu, Z.; Devadoss, C.; Moore, J. S.; Kopelman, R. "Directed Energy Transfer Funnels in Dendrimeric Antenna Supermolecules." J. of Phys. Chem. B 1997, 101(31), 6318-6322.

Xu, Z.; Moore, J. S. "Design and synthesis of a convergent and directional molecular antenna." Acta. Polym. 1994, 45(2), 83-87.

Future Trends in Microelectronics. Reflections on the Road to Nanotechnology; Luryi, S., Xu, J., and Zaslaysky, A., Eds.; Kluwer Academic: Dordrecht, 1999; Volume 323.

Prospects in Nanotechnology. Toward Molecular Manufacturing; Krummenacker, M. and Lewis, J., Eds.; Wiley: New York, 1995.

Barnes, W. L.; Samuel, I. D. W. "Reflections on Polymers." Science 1999, 285(July 9), 211-212.

Fendler, J. H.; Fendler, E. J. Catalysis in Micellar and Macromolecular Systems; Academic Press: New York, 1975.

Fendler, J. H. "Membrane-Mimetic Approach to Advanced Materials" Springer-Verlas: Berline, 1994; Chapter 113, p. 225.

Newkome, G. R.; Moorefield, C. N.; Keith, J. M.; Baker, G. R.; Escamilla, G. H. "Chemistry Within a Unimolecular Micelle Precursor. Boron Superclusters by Site- and Depth-Specific Transformations of Dendrimers." Angew. Chem. 1994, 106(6), 701-703.

Newkome, G. R.; Moorefield, C. N.; Keith, J. M.; Baker, G. R.; Escamilla, G. H. "Chemistry Within a Unimolecular Micelle Precursor: Boron Superclusters by Site- and Depth-Specific Transformations of Dendrimers." Angew. Chem., Int. Ed. Engl, 1994, 33(6), 666-668.

Newkome, G. R.; Narayanan, V. V.; Patri, A.; Groβ, J.; Moorefield, C. N.; Baker, G. R. "Cascade infrastructure Modification Via Integration of Application-Based Monomers." Polym. Mater. Sci. Eng. 1995, 73, 222-223.

Newkome, G. R.; Patri, A. K.; Godinez, L. A. "Design, Syntheses, Complexation and Electrochemistry of Polynuclear Metallodendrimers Possessing Internal Metal Binding Loci." Chem. Eur. J. 1999, 5(5), 1445-1451.

Newkome, G. R.; He, E.; Godinez, L. A. "Construction of Dendritic Assemblies: A Tailored Approach to Isomeric Metallomacromolecules by Means of Bis(2,2,':6',2"-terpyridine)ruthenium(II) Connectivity." Macromolecules 1998, 31, 4382-4386.

Zhao, M.; Crooks, R. M. "Dendrimer-Encapsulated Pt Nanoparticles: Synthesis, Characterization, and Applications to Catalysis." Adv. Mater. (Weinheim, Fed. Repub. Ger.) 1999, 11(3), 217-220.

Chechik, V.; Zhao, M.; Crooks, R. M. "Self-Assembled Inverted Micelles Prepared from a Dendrimer Template: Phase Transfer of Encapsulated Guests.: J. Am. Chem. Soc. 1999, 121, 4910-4911.

Zhao, M.; Crooks, R. M. "Homogeneous Hydrogenation Catalysis with Monodisperse, Dendrimer-Encapsulated Pd and Pt Nanoparticies." Angew. Chem. Int. Ed. 1999, 38(3), 364-366.

Balogh, L.; Tomalia, D. A. "Poly(Amidoamine) dendrimer-Tamplated Nanocomposites. 1. Synthesis of Zerovalent Copper Nanoclusters." J. Am. Chem. Soc. 1998, 120, 7355-7356.

Tan, N. C. B.; Balogh, L.; Trevino, S. F.; Tomalia, D. A.; Lin, J. S. "A small angle scattering study of dendrimer-copper sulfide nanocomposites." Polymer 1999, 40, 2537-2545.

Dagani, R. "Jewel-studded molecular trees." Chem. & Eng. News 1999, 77(6), 33-36.

Kriesel, J. W.; Tilley, T. D. "Dendrimers as Building Blocks for Nanostructured Materials Micro- and Mesoporosity in Dendrimer-Based Xerogels." Chem. Mater. 1999, 11, 1190-1193.

Long, J. W.; Swider, K. E.; Merzbacher, C. I.; Rolison, D. R. "Voltammetric Characterization of Ruthenium Oxide-based Aerogels: the Nature of Capacitance in Nanostructured Materials." Technical Report #4, 7 Jul. 1999; Office of Naval Research: Washington, D.C., Grant N00014-99-WX-20324.

Tran Van, F.; Delabouglise, D. "Polyethyleneoxide-dihydrophenazine block copolymer as a cathode material for lithium-polymer batteries." Electrochim. Acta 1998, 43 (14-15), 2083-2087.

Steigerwald, Brus, L. E. "Semiconductor Crystallites: A Class of Large Molecules." Acc. Chem. Res, 1990, 23(6), 183-188.

Noglik, H.; Pietro, W. J. "Surface Functionalization of Cadium Sulfide Quantum Confined Semiconductor Nanoclusters. 2. Formation of a "Quantum Dot" Condensation Polymer." Chem. Mater. 1995, 7(7), 1333-1336.

Que, W.-M.; Kirczenow, G. "Theory of collective excitations in a two-dimensional array of quantum dots." Phys. Rev. B: Condens. Matter 1988, 38(5), 3614-3615.

Que, W.-M.; Kirczenow, G. "Theory of collective excitations in a two-dimensional array of quantum dots." Phys. Rev. Lett. 1990, 64(25), 3100-3101.

Weller, H. "Colloidal Semiconductor Q-Particles: Chemistry in the Transition Region Between Solid State and Molecules." Angew. Chem., Int. Ed. Engl. 1993, 32, 41-53.

What is claimed is:

1. A compound of the formula

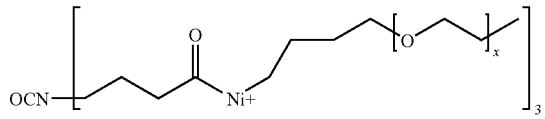

Wherein x is an integer from 1 to 4.

2. A method of making the compound of claim 1 by reacting monomethylated glycol with a nitrotrichloride

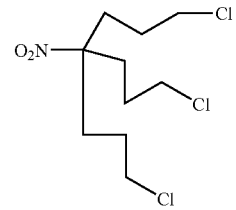

And producing nitrotris (triethylene glycol); reducing the product to a corresponding amine; and treating the amine with phosgene or a phosgene equivalent to produce an isocyanate.

3. A method as defined in claim 2 further including the steps of coupling the amine with nitrotris (acid chloride) and then reducing the nitromoiety and treating with phosgene to produce a second generation dendron.

* * * * *